United States Patent [19]

Carroll et al.

[11] 4,076,120

[45] Feb. 28, 1978

[54] CARTRIDGE FOR HOLDING HEMOSTATIC CLIPS

[75] Inventors: Ronald L. Carroll, Evanston; John S. Ziegler, Arlington Heights, both of Ill.

[73] Assignee: American Hospital Supply Corporation, Evanston, Ill.

[21] Appl. No.: 749,292

[22] Filed: Dec. 10, 1976

[51] Int. Cl.² .............................................. B65D 85/54
[52] U.S. Cl. .................................... 206/339; 128/325; 206/63.3; 206/340; 206/804
[58] Field of Search ..................... 128/325; 221/312 R, 221/312 C; 206/63.3, 228, 229, 334, 336, 337, 339, 340, 341, 348, 355, 356, 370, 490, 572, 804

[56] References Cited

U.S. PATENT DOCUMENTS

| | | | |
|---|---|---|---|
| 3,232,089 | 2/1966 | Samuels et al. | 206/341 |
| 3,270,745 | 9/1966 | Wood | 128/325 |
| 3,326,216 | 6/1967 | Wood | 128/325 |
| 3,363,628 | 1/1968 | Wood | 206/339 |
| 3,713,533 | 1/1973 | Reimels | 206/339 |
| 3,797,657 | 3/1974 | Petrillo | 206/356 |
| 3,835,532 | 9/1974 | Petrillo | 206/356 |

FOREIGN PATENT DOCUMENTS

2,405,175   8/1974   Germany .............................. 206/355

Primary Examiner—George E. Lowrance
Assistant Examiner—Bruce H. Bernstein

[57] ABSTRACT

A cartridge for holding hemostatic clips comprises an outer casing and an elongated body positioned within the casing. The body includes a plurality of sets of pairs of walls on each side of a longitudinal line along the body. Each pair of walls defines a clip-receiving compartment between the walls, and each compartment is transversely aligned with a compartment on the other side of the longitudinal line so that each end of a generally U-shaped hemostatic clip can be received in one of the transversely aligned compartments. The walls of each pair of walls are flexible away from each other so that a clip can be removed by inserting the jaws of applying forceps between the walls and over the clip to flex the walls apart.

10 Claims, 18 Drawing Figures

CARTRIDGE FOR HOLDING HEMOSTATIC CLIPS

BACKGROUND AND SUMMARY

This invention relates to a cartridge for holding hemostatic clips, and, more particularly, to a cartridge which holds a plurality of clips between pairs of walls until the walls are flexed apart by inserting the jaws of a forceps between the walls.

Hemostatic clips are used to ligate or clamp blood vessels during surgical procedures. Such clips are generally C-shaped or U-shaped and are positioned over the vessel by an instrument called an applying forceps. The clip is held between the jaws of the forceps, and when the clip is properly positioned, the jaws are squeezed to clamp the clip over the vessel to close the vessel.

Hemostatic clips are often packaged in cartridges or clip supports which hold a number of clips in a manner which permits each individual clip to be captured and picked up by the jaws of the forceps. Such cartridges are shown in, for example, U.S. Pat. Nos. 3,270,745, 3,326,216, 3,363,628, and 3,463,156. Problems with prior art cartridges include clips falling from the cartridge prior to use and improper or difficult transfer of the clip from the cartridge to the forceps.

The invention provides a cartridge which holds a number of clips between separate compartment-forming walls. Each clip is frictionally retained between the walls of each compartment, and the walls are flexed apart by the jaws of the forceps to release a single clip when the jaws are inserted over the clip. The captured clip can then be withdrawn by the forceps, and the remaining clips are retained securely within the cartridge.

DESCRIPTION OF THE DRAWING

The invention will be explained in conjunction with an illustrative embodiment shown in the accompanying drawing, in which.

DESCRIPTION OF SPECIFIC EMBODIMENT

Figures 1, 3:
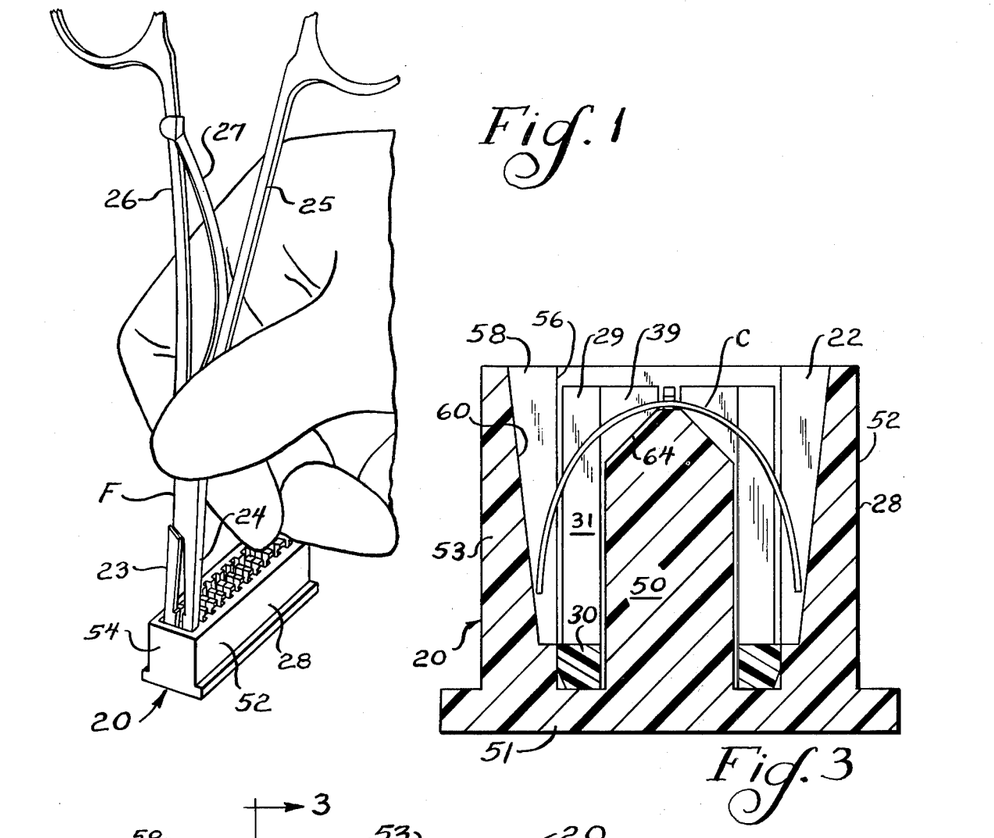
FIG. 1 is a perspective view of a hemostatic clip cartridge formed in accordance with the invention and a pair of forceps inserted into the cartridge to pick up one of the clips.
FIG. 3 is a sectional view taken along the line 3—3 of FIG. 2.
Figure 2:
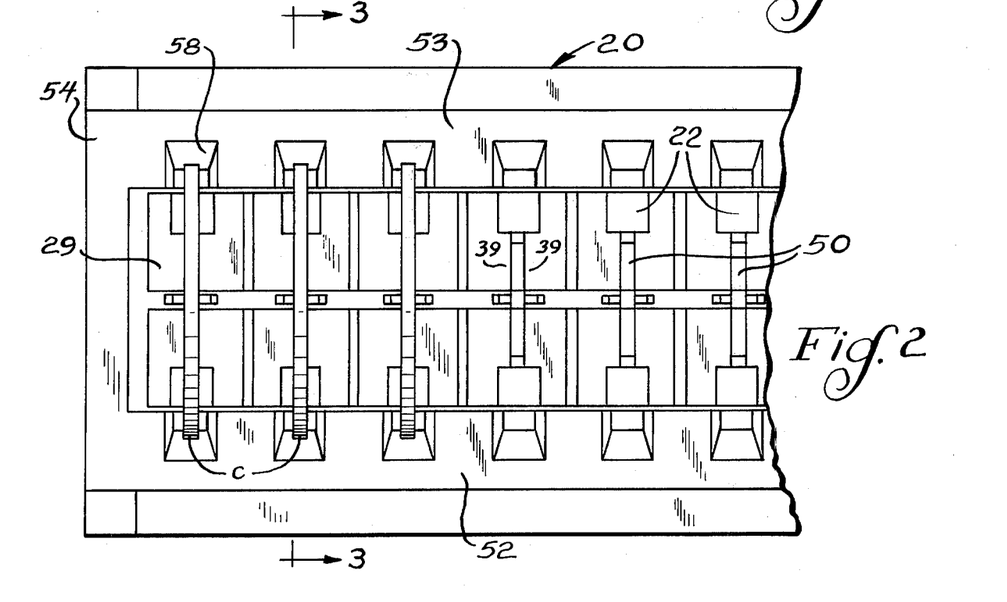
FIG. 2 is a fragmentary top plan view of the cartridge, with hemostatic clips shown in the first three compartments of the cartridge.
Figure 14:
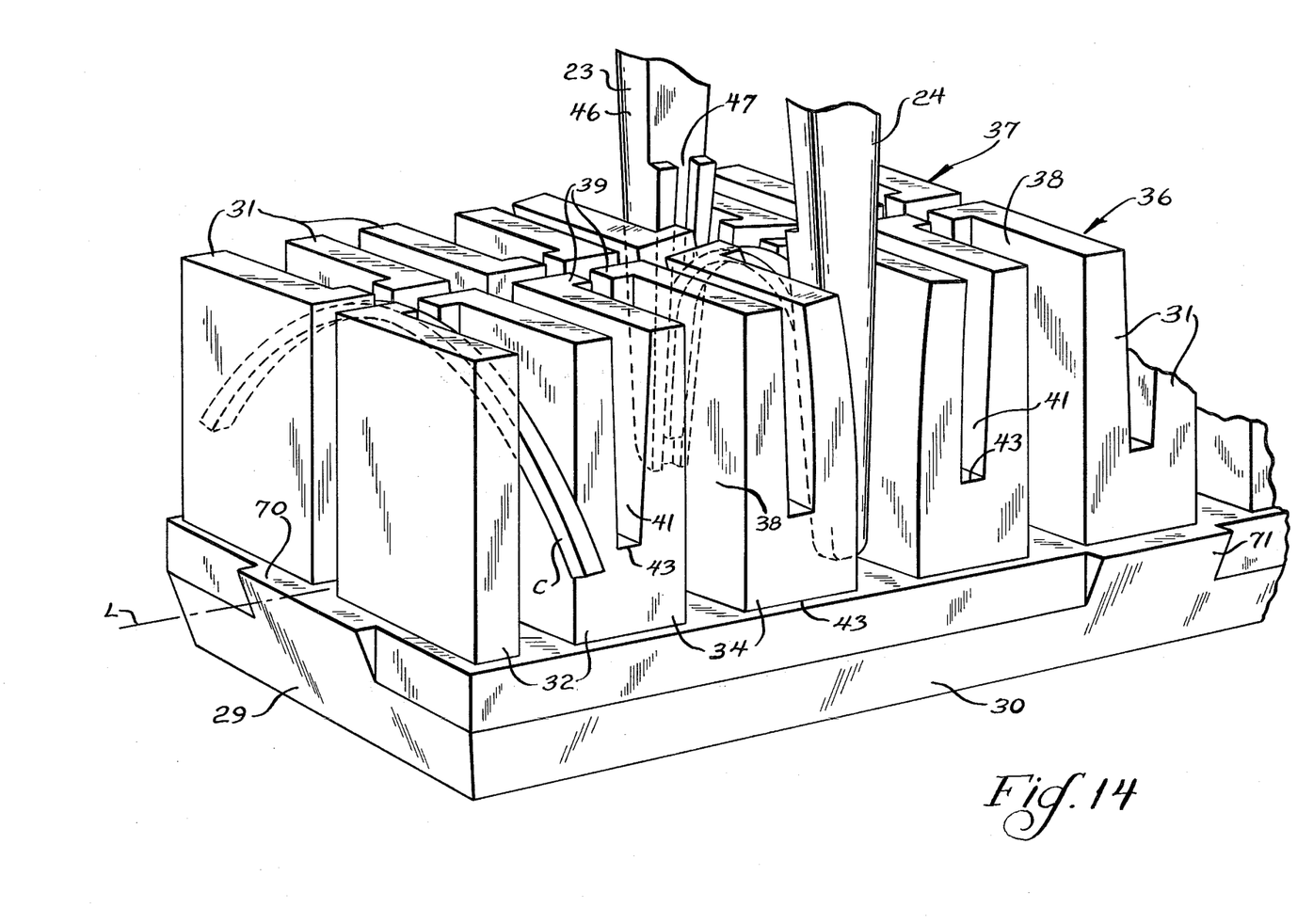
FIG. 14 is a fragmentary perspective view of the inner body of the cartridge showing the jaws of an applying forceps inserted between the walls of a clip compartment to spread the walls and to capture the clip.

Referring first to FIGS. 1-3, the numeral 20 designates generally a cartridge for holding hemostatic clips C. The cartridge is elongated and is provided with a plurality of longitudinally spaced clip-receiving compartments 22, and, for purposes of clarity, hemostatic clips C are shown in only the first three compartments on the left side of FIG. 2. Each clip can be individually captured and removed from the cartridge by a pair of applying forceps F. The forceps includes a pair of jaws 23 and 24 which are continuations of handles 25 and 26, respectively. The jaws are maintained in an open, spaced-apart position by a spring 27 which separates the handles, and the jaws can be inserted over a clip merely by pushing the ends of the jaws into a clip compartment as shown in FIG. 1. The cartridge 20 comprises an outer open-topped boxlike casing 28 and an inner body 29 which is snapped into the outer casing. A perspective view of the inner body is shown in FIG. 14, and the inner body is seen to include an elongated base portion 30 and a plurality of walls 31 which extend upwardly from the base. The walls are spaced both in the longitudinal direction along the body and are also spaced-apart on opposite sides of a longitudinal line L (see also FIG. 7) which lies along the approximate longitudinal center line of the body. The walls 31 are arranged in pairs 32, 33, 34, 35, etc., and the longitudinal line L divides the pairs into a first set 36 which lies on one side of the longitudinal line and a second set 37 which lies on the other side of the longitudinal line.

Each pair of walls forms a compartment 38 for receiving one of the ends of a hemostatic clip, and the compartments of two pairs of walls on opposite sides of the longitudinal line L are aligned so that a clip transversely straddles the longitudinal line when the ends thereof are received in the aligned compartments. The width of each compartment is narrowed adjacent the longitudinal line by shoulder portions 39 of the walls, which provide each wall with a generally L shape in horizontal cross section. The shoulder portion 39 of each wall of a particular pair of walls extends in the longitudinal direction toward the other wall of that pair, and the spacing between the confronting surfaces of these shoulder portions is slightly less than the width of the clip so that the clip is frictionally retained by these confronting surfaces. If desired, for example, because of the shape of the clip, the spacing between the shoulders 39 of one of the pairs of walls can be greater than the width of the clip so that the clip is frictionally retained by only one pair of shoulders 39.

Figure 7:
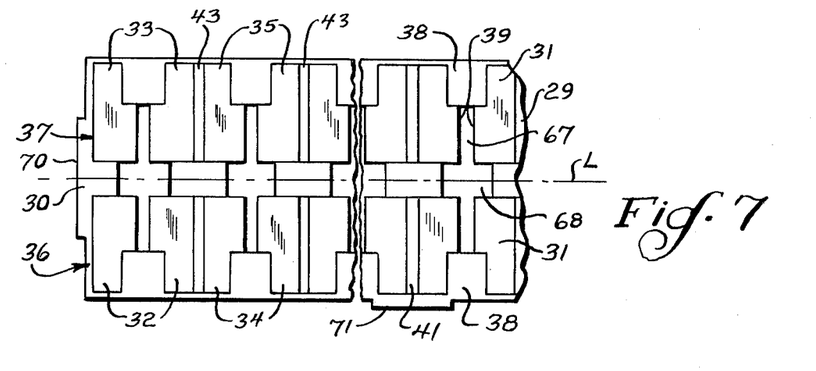
FIG. 7 is a fragmentary top plan view of the inner body of the cartridge.
Figure 8:
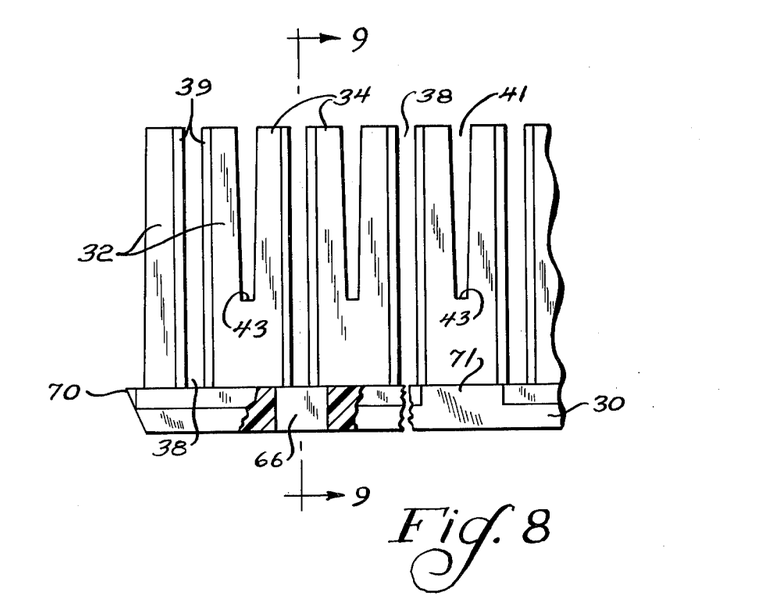
FIG. 8 is a fragmentary elevational view, partially broken away, of the inner body of the cartridge.
Figure 9:
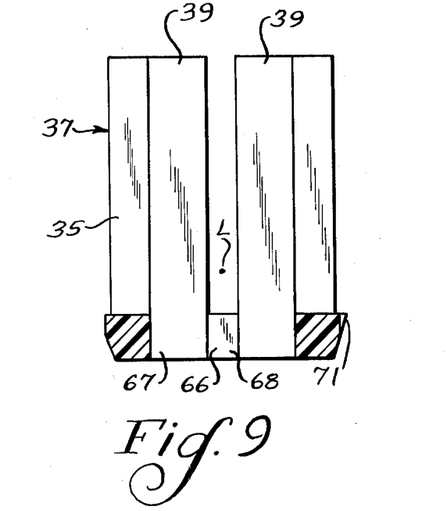
FIG. 9 is a sectional view taken along the line 9—9 of FIG. 8.
Figure 10:
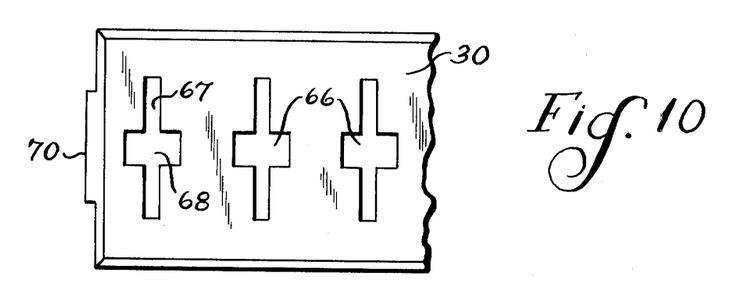
FIG. 10 is a fragmentary bottom plan view of the inner body of the cartridge.
Figure 11:
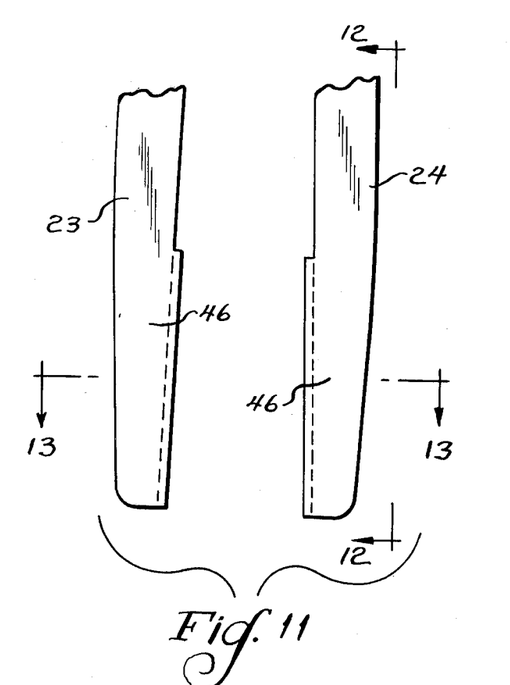
FIG. 11 is a fragmentary side view of the jaws of an applying forceps.
Figure 12:
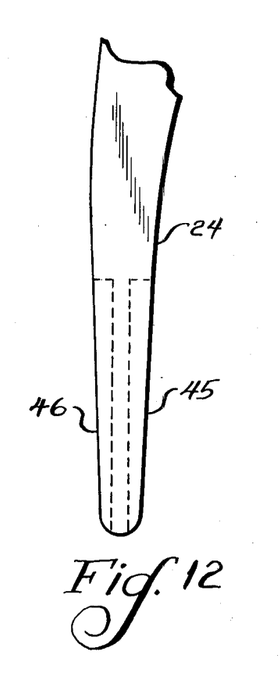
FIG. 12 is a fragmentary view of the forceps jaws taken along the line 12—12 of FIG. 11.
Figure 13:
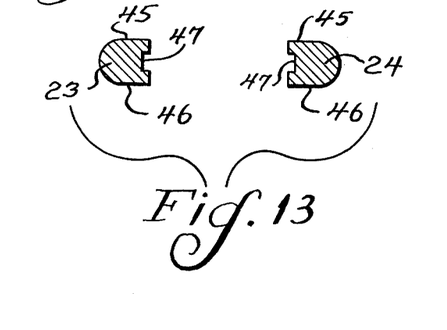
FIG. 13 is a sectional view taken along the line 13—13 of FIG. 11.

The adjacent walls of adjacent pairs of walls in the sets 36 and 37 are spaced apart for about half of the distance between the upper ends of the walls and the base 30, this spacing being indicated by the numeral 41 in FIGS. 7 and 14. In the particular embodiment illustrated, the lower portions of adjacent walls of adjacent sets are joined by a connecting portion 43 (FIGS. 14-16) in order to increase the stiffness of the clamping walls.

The cartridge 20 is capable of being used with almost any type of hemostatic clip. Most of such clips are generally U-shaped or C-shaped, and a typical clip C is illustrated in FIG. 14. Hemostatic clips are conventionally formed of flexible material which has some resilience but which can also be permanently deformed by squeezing the applying forceps. Most hemostatic clips are made from metal. The clip is positioned within the inner body so that the ends of the clip are positioned in transversely aligned compartments 38. The central portion of the clip passes between the confronting surfaces of the opposed shoulder portions 39 of each pair of walls which define the clip-receiving compartments, and the clip is frictionally retained thereby.

Figure 15:
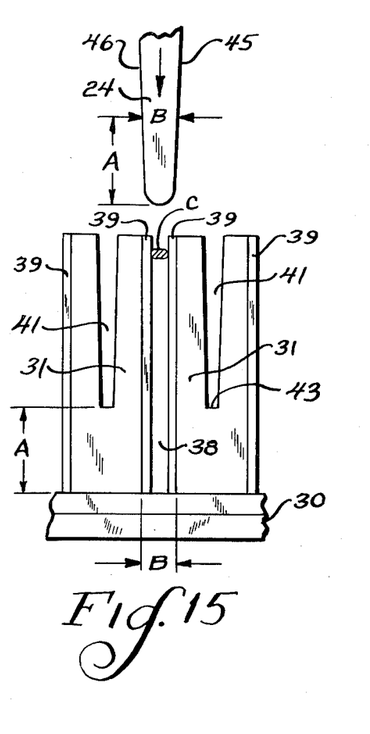
FIG. 15 is a fragmentary elevational view of the inner body, with a clip shown in cross section, and the jaws of an applying forceps about to be inserted between the walls of a clip compartment.
Figure 16:
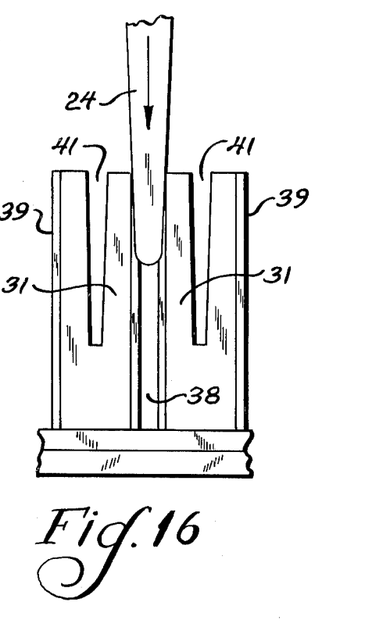
FIG. 16 is a view similar to FIG. 15 showing the jaws of the forceps partially inserted between the walls of a clip compartment.
Figure 17:
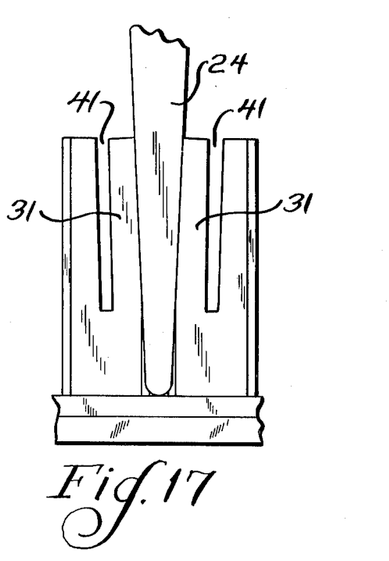
FIG. 17 is a view similar to FIGS. 15 and 16 showing the jaws of the forceps fully inserted between the walls of a clip compartment to spread the walls and to capture the clip.

Referring to FIGS. 15-17, a clip is captured by the forceps and removed from the cartridge by pushing the open jaws into the transversely aligned compartments 38 in which the clip is positioned. The inner body 29 is adapted for use with applying forceps whose jaws have tapered or upwardly diverging side surfaces 45 and 46, and as the jaws are inserted into the compartments 38 between an associated pair of walls 31, the walls are forced away from each other. The inner body is formed of a material which will provide the walls with sufficient flexibility to accommodate the wedging action of the forceps, and in one specific embodiment of the cartridge, both the inner body and the outer casing were formed of heat-resistant medical polyphenylene oxide. The spacing 41 between adjacent walls of adjacent pairs of the sets 36 and 37, respectively, permit the walls of each pair to flex or spread apart independently of the walls of adjacent pairs, and such flexing is not inhibited by the adjacent walls. As can be seen best in FIG. 14, each of the jaws of the forceps is provided with a longitudinally extending central groove 47 having a width approximately the same as the width of the clip, and the two ends of the clip are positioned within the grooves of the jaws as the forceps is pushed downwardly.

Referring to FIG. 15, the taper of the forceps jaws is such that the width of the tapered jaws at a distance A from the ends of the jaws, which corresponds to about ¼ or ⅓ of the height of the clip compartments 38, is approximately the same as the spacing B between the walls. When the jaws are inserted a distance greater than A, the jaws begin to force the walls apart as in FIG. 16, and eventually the shoulders 39 of the walls will be forced out of frictional engagement with the clip. When the jaws are completely inserted (FIG. 17), the clip is free of the shoulders 39 and is captured within the grooves of the jaws. When the forceps jaws are withdrawn from the cartridge, the clip will be withdrawn with the forceps and will be in position within the jaws to be applied by the forceps without further manipulation. The resilient walls will return to their original positions as the forceps is withdrawn, but the walls will be prevented from contacting the clip by the jaws.

Figure 18:
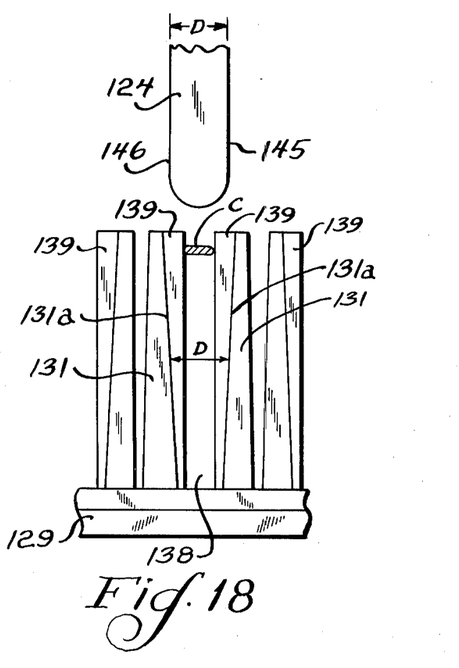
FIG. 18 is a view similar to FIG. 15 showing a modified inner body for use with forceps having straight-sided jaws.

FIG. 18 illustrates a modified embodiment of the inner body, designated 129, for use with forceps 124 whose side surfaces 145 and 146 are not tapered. The walls 131 of the body 129 are identical to the walls 31 of the body 29, but the surfaces 131a thereof which define the clip-receiving compartments diverge upwardly so that the spacing between the upper ends of the surfaces 131a is greater than the thickness of the jaws. The jaws will engage these surfaces and spread the walls 131 as the jaws are pushed downwardly into the compartments, thereby releasing the clip C from between the shoulder portions 139 of the walls.

In the particular embodiment illustrated in FIG. 18, the width of the jaws is equal to the spacing D between the diverging surfaces 131a at about one-half the height of the clip compartment. In this embodiment the surfaces 131a would begin to be spread apart when the jaws were inserted about halfway down into the compartment.

Returning to the embodiment illustrated in FIGS. 2-3, the inner body 29 is positioned within the outer casing 28, and the inner body and the casing cooperate to form the clip-receiving compartments 22. The outer casing also includes upwardly extending projections or support fingers 50 (FIGS. 2 and 3), each of which supports the midportion of a clip and prevents the clip from being moved downwardly as the jaws of the forceps are pushed downwardly over the clip.

Figure 4:
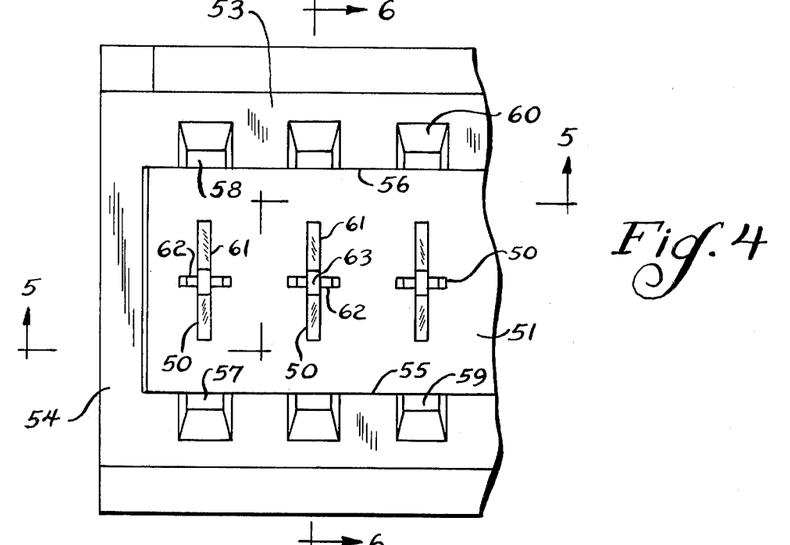
FIG. 4 is a fragmentary top plan view of the outer casing of the cartridge.
Figure 5:
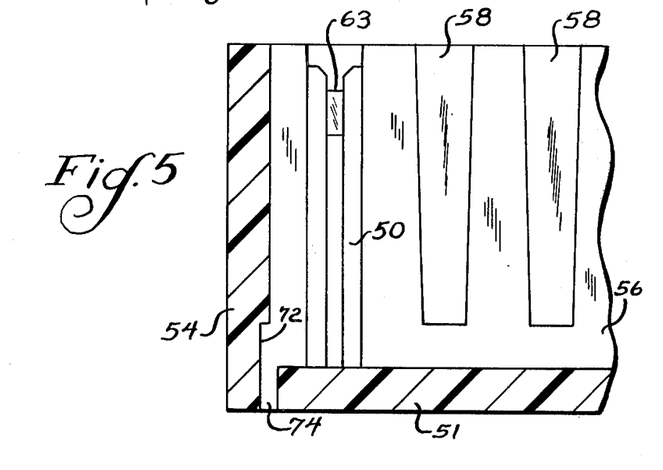
FIG. 5 is a fragmentary sectional view taken along the line 5—5 of FIG. 4.

The outer casing includes a bottom wall or base 51 (FIGS. 3-5), a pair of longitudinally extending side walls 52 and 53, and a pair of transversely extending end walls 54. Each of the side walls 52 and 53 includes an inner surface 55 and 56, respectively (FIG. 4), each of which is provided with a plurality of transversely outwardly extending generally channel-shaped recesses 57 and 58, respectively. The recesses 57 and 58 are transversely aligned with the clip-receiving compartments 22 of the inner body. In the embodiment illustrated, the outer surface 60 of the recesses 57 and 58 slant inwardly from top to bottom so that the transverse dimension of the recesses decreases toward the bottom. The slanted surfaces are advantageous in guiding the forceps jaws, but these surfaces can be vertical if desired.

Figure 6:
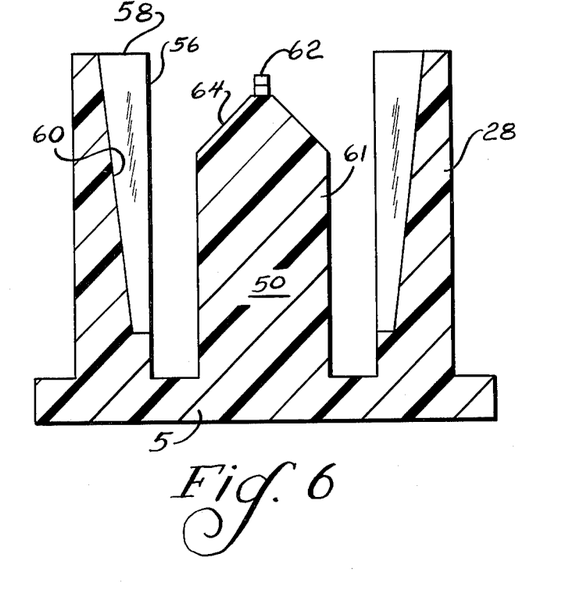
FIG. 6 is a sectional view taken along the line 6—6 of FIG. 4.

A support finger 50 extends upwardly from the base 51 of the outer casing in alignment with each pair of transversely aligned recesses 57 and 58. Each support finger is generally cruciform in horizontal cross section and includes a transversely extending portion 61 (FIG. 4) and a longitudinally extending portion 62. The upper end of each longitudinal portion is provided with a central notch 63 for receiving and supporting the midportion of a hemostatic clip, and the upper edge 64 (FIGS. 3 and 6) of the transverse portion diverges downwardly to accommodate the curvature of the clip.

Referring now to FIGS. 7-10, the base 30 of the inner body is provided with a cruciform opening 66 for each of the support fingers 50 of the outer casing. When the inner body is positioned within the outer casing, the base 30 is supported by the bottom wall 51 of the outer casing (FIG. 3), and the support fingers extend upwardly through the openings 66. Each of the openings includes a transverse portion 67 which is aligned with the space between a pair of confronting shoulder portions 39 of the walls 36 and 37 and a longitudinally extending portion 68 which is aligned with the longitudinal line L. The transverse portion 61 of each support finger will therefore be positioned between a pair of confronting shoulder portions of the walls, and the longitudinal portion 62 of the support finger will be positioned along the line L within the space between the two sets 36 and 37 of walls. The width of the transverse portion 61 is less than the spacing between the shoulders 39 so that the support fingers do not hold the shoulders apart.

The inner body is retained within the outer casing by an outwardly extending ledge 70 (FIGS. 7 and 8) on each end of the base of the body and an outwardly extending ledge 71 (FIG. 7) on the side of the base below the set 36 of walls. Each of the end walls 54 of the outer casing is provided with a recess 72 (FIG. 5) for receiving and retaining the ledges 70, and the side wall is provided with a similar recess for receiving and retaining the ledge 71. Opening 74 extends through the bottom wall of the casing below the recess 72 to permit the casing to be injection molded. The inner body 29 can also be injection molded.

The assembled cartridge provides a plurality of clip-receiving compartments which firmly hold the clips in the cartridge until each clip is removed by the forceps. Each compartment includes a first pair of walls which frictionally retain one end of a clip, a second pair of walls independent from the first pair which frictionally retains the other end of the clip, and a support finger for supporting and centering the clip as the jaws of the forceps move downwardly over the clip to capture it. When the clip has been captured, the wedging action of the jaws will have forced the walls out of contact with the ends of the clip to permit the clip to be freely removed without interference from the walls. Each pair of walls can be wedged apart independently of adjacent walls so that the removal of a clip is not interfered with by, and does not interfere with, adjacent walls and adjacent clips. The confronting shoulder portions of the walls and the recess in the support finger center the clip in the clip-receiving compartment as the jaws of the forceps are guided downwardly by the walls of the recesses 57 and 58 of the outer casing and the walls 31 of the inner body, thereby insuring that the clip will be positioned within the grooves 47 of the forceps jaws and captured.

While in the foregoing specification a detailed description of a specific embodiment of the invention was set forth for the purpose of illustration, it is to be understood that many of the details hereingiven may be varied considerably by those skilled in the art without departing from the spirit and scope of the invention.

We claim:

1. A cartridge for holding a plurality of articles in a manner which permits the articles to be individually removed, the cartridge comprising an elongated base, a pair of spaced-apart longitudinally extending outer walls extending upwardly from the base, a plurality of sets of inner walls extending upwardly from the base between transversely to the spaced-apart outer walls, each of the sets of inner walls including a pair of holding walls which are spaced apart in the longitudinal direction of the base and which provide a compartment for receiving one of said articles, the longitudinal spacing between the holding walls being such that the article is frictionally retained between the holding walls, and means for supporting the article within the compartment, each of the holding walls being formed of flexible material and being flexible away from each other when an article is removed from a compartment by inserting an instrument between the holding walls of the compartment and over the article, the instrument bearing upon the walls so as to force the walls apart and release their grip upon the article, thereby allowing the article to be removed without resistance.

2. The cartridge of claim 1 in which each of said sets of inner walls includes a second pair of holding walls which are spaced apart in the longitudinal direction of the base, each of the holding walls of the second pair being transversely aligned with one of the walls of the first-mentioned pairs of holding walls of the set.

3. The cartridge of claim 2 in which said second pair of holding walls of each of said sets is spaced apart in a transverse direction from the first-mentioned pairs of holding walls of the set.

4. The cartridge of claim 1 in which the supporting means for each compartment comprises a projection extending upwardly from the base and aligned with the compartment.

5. The cartridge of claim 4 in which each projection is provided with a recess in the upper end thereof for receiving one of said articles and for centering said article with respect to the aligned compartment.

6. The cartridge of claim 1 in which each of the holding walls of each set is generally L-shaped in a cross section taken parallel to the base and includes a shoulder portion which extends toward the other holding wall of the set.

7. The cartridge of claim 1 in which the cartridge is formed from an outer casing and an inner body positioned within said outer casing, the outer casing including said pair of outer walls and said base and the inner body including said sets of inner walls.

8. The cartridge of claim 7 in which said inner body includes a base portion which is supported by the base of the outer casing and which is provided with an opening therethrough between the pair of holding walls of each of said sets, the supporting means for each compartment comprising a projection extending upwardly from the base of the outer casing and through one of the openings in the base of the inner body.

9. A cartridge for holding a plurality of hemostatic clips in a manner which permits the clips to be individually removed by forceps, the cartridge comprising an elongated outer casing having a perimetric outer wall extending upwardly from the base, an inner body having a base portion supported by the base of the outer casing and a plurality of sets of inner walls extending upwardly from the base portion, each of the sets of inner walls including a first pair of holding walls on one side of a line extending longitudinally along the base portion which are spaced apart in the longitudinal direction of the base and which provide a compartment therebetween for receiving an end of a generally U-shaped hemostatic clip and a second pair of holding walls on the other side of said longitudinally extending line which are spaced apart in the longitudinal direction of the base and which provide a compartment for receiving the other end of a generally U-shaped hemostatic clip, each of the compartments on one side of said longitudinally extending line being transversely aligned with a compartment on the other side of the longitudinally extending line whereby when a hemostatic clip is received by a pair of transversely aligned compartments it straddles said longitudinally extending line, and means associated with each pair of transversely aligned compartments for supporting the midportion of a hemostatic clip, each of the holding walls of each pair of holding walls being flexible away from each other when a hemostatic clip is removed from a pair of transversely aligned compartments by inserting the jaws of a forceps between the walls of the compartments and over the clip, the jaws of the forceps bearing upon the walls so as to force the walls apart and release the grip upon the clip, thereby allowing the clip to be removed without resistance.

10. The cartridge of claim 9 in which each of the holding walls of each pair is generally L-shaped in a cross section taken parallel to said base portion of the inner body and includes a shoulder portion which extends toward the other holding wall of the pair.

* * * * *

UNITED STATES PATENT AND TRADEMARK OFFICE
CERTIFICATE OF CORRECTION

PATENT NO. : 4,076,120

DATED : February 28, 1978

INVENTOR(S) : Ronald L. Carroll et al

It is certified that error appears in the above-identified patent and that said Letters Patent are hereby corrected as shown below:

In column 5, line 58, insert --and-- before "transversely".

*Signed and Sealed this*

*Twenty-seventh* Day of *June 1978*

[SEAL]

*Attest:*

RUTH C. MASON
*Attesting Officer*

DONALD W. BANNER
*Commissioner of Patents and Trademarks*